United States Patent [19]

Sasaki et al.

[11] Patent Number: 5,482,723
[45] Date of Patent: Jan. 9, 1996

[54] LACTIC ACID BACTERIA, ANTIBACTERIAL SUBSTANCE PRODUCED BY THE BACTERIA, FERMENTED MILK STARTER CONTAINING THE BACTERIA, AND PROCESS FOR PRODUCING FERMENTED MILK BY USING THE STARTER

[75] Inventors: Masahiro Sasaki, Higashimurayama; Satoshi Ishii; Yoshihiko Yamauchi, both of Sapporo; Katsushi Kitamura, Yamanashi; Shuji Toyoda; Kenkichi Ahiko, both of Sapporo, all of Japan

[73] Assignee: Snow Brand Milk Products Co., Ltd., Hokkaido, Japan

[21] Appl. No.: 987,082

[22] Filed: Dec. 7, 1992

Related U.S. Application Data

[63] Continuation of Ser. No. 658,031, Feb. 22, 1991, abandoned.

[30] Foreign Application Priority Data

Feb. 23, 1990 [JP] Japan ..................... 2-44067
Jan. 26, 1991 [JP] Japan ..................... 3-041443

[51] Int. Cl.⁶ ..................................... A23C 23/00
[52] U.S. Cl. ................. 426/43; 426/40; 426/583
[58] Field of Search .................... 426/43, 34, 36, 426/42, 580, 582, 583

[56] References Cited

U.S. PATENT DOCUMENTS

| | | | |
|---|---|---|---|
| 4,034,115 | 7/2977 | Roberts | 426/43 |
| 4,339,464 | 7/1982 | Vedamuthu | 426/43 |
| 4,855,147 | 8/1989 | Yokota et al. | 426/43 |
| 4,888,183 | 12/1989 | Kondou | 426/43 X |

FOREIGN PATENT DOCUMENTS

| | | |
|---|---|---|
| 62-239 | 1/1987 | Japan . |
| 63-7743 | 1/1988 | Japan . |

OTHER PUBLICATIONS

Pulusani et al., Journal of Food Science, vol. 44, No. 2, pp. 575–578 (1979).
Dempster et al., Archives of Oral Biology, vol. 27, No. 2, pp. 151–157 (1982).
Klaenhanner, Biochimie 70, pp. 337–349 (1988).
CA 112:6353v (1990).
CA 95:217378a (1981).

*Primary Examiner*—Carolyn Paden
*Attorney, Agent, or Firm*—Millen, White, Zelano, & Branigan

[57] ABSTRACT

Disclosed herein are *Streptococcus salivarius* subsp. *thermophilus* and variants thereof capable of producing an antibacterial substance which is a peptide or protein or a conjugate thereof, the antibacterial substance produced by the bacteria, and processes for producing fermented milk by using any one of the bacteria as a starter. The lactic acid bacteria produce the antibacterial substance, so that use of any one of the lactic acid bacteria as a starter for fermented milk inhibits growth of another lactic-acid-forming lactic acid bacteria also used as a starter owing to the antibacterial substance produced during fermentation. It is therefore possible to suppress the formation of the acid during storage or transportation of fermented milk, thereby making it possible to prevent taste and flavor variations and quality deterioration of the product.

8 Claims, 2 Drawing Sheets

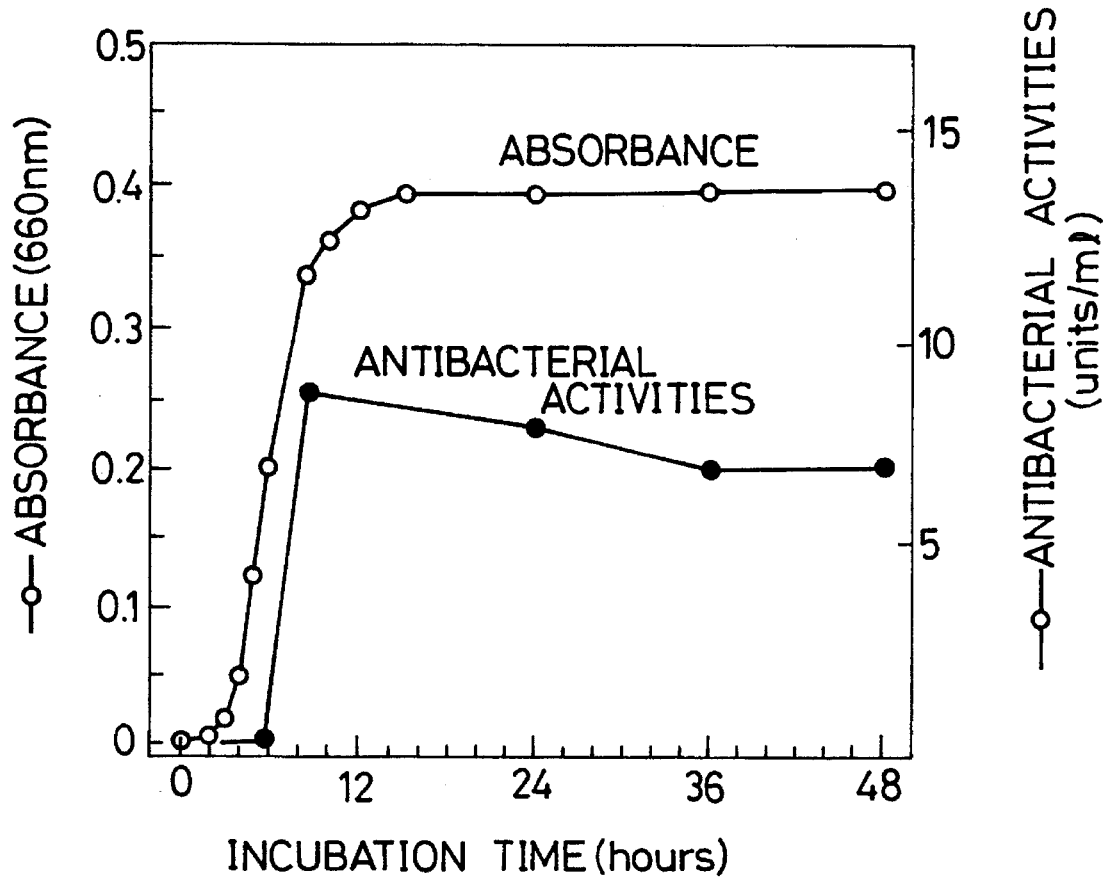

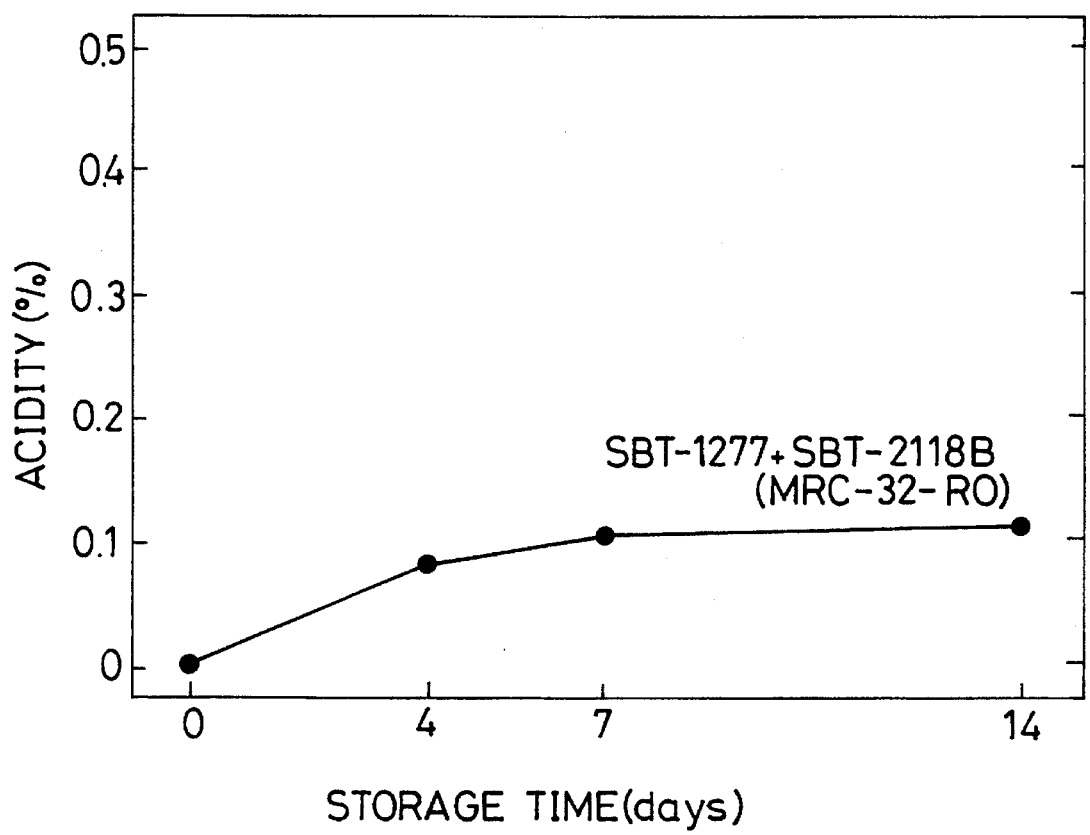

LACTIC ACID BACTERIA, ANTIBACTERIAL SUBSTANCE PRODUCED BY THE BACTERIA, FERMENTED MILK STARTER CONTAINING THE BACTERIA, AND PROCESS FOR PRODUCING FERMENTED MILK BY USING THE STARTER

This application is a continuation of application Ser. No. 07/658,031, filed Feb. 22, 1991, now abandoned.

BACKGROUND OF THE INVENTION

1. Field of the Invention

The present invention relates to novel lactic acid bacteria belonging to the genus *Streptococcus salivarius* subsp. *thermophilus* and variants thereof.

This invention is also concerned with a novel antibacterial substance produced by the above lactic acid bacteria or any one of the above variants.

Further, the present invention pertains to fermented milk starters comprising the above lactic acid bacteria or any one of the above variants and also to processes for producing fermented milk whose acidity increase during storage or transportation is reduced, said processes making use of any one of the fermentation starters.

2. Description of the Related Art

A variety of thermophilic bacteria are found in milk and milk products. They are lactic acid bacteria useful as starters for yogurt or cheese. Among these, some thermophilic bacteria are known to produce a low molecular, antibacterial substance having a molecular weight not higher than 700 [Pulusani, S. R., et al., "Journal of Food Science", 44 575 (1979)]. However, there have not been known yet any thermophilic bacteria which produces a high-molecular, antibacterial substance composed of a protein or peptide or a conjugate thereof as in the present invention.

The term "thermophilic bacteria" as used herein is a generic term for the known bacteria which belong to the genus *Streptococcus salivarius* subsp. *thermophilus*. On the other hand, the term "antibacterial substances" as employed herein does not mean the known low-molecular compounds having antibacterial activities such as organic acids—for example, lactic acid—and hydrogen peroxide but is a generic term for substances composed of a peptide, a protein or a conjugate thereof and having antibacterial activities.

In general, antibacterial substances produced by lactic acid bacteria are used to enhance the storability of foods or to avoid deterioration in quality of foods due to their contamination by saprophytes, as typified by nisin produced by certain *Lactococcus lactis* subsp. *lactis* (formerly, *Streptococcus lactis* subsp. *lactis*).

In the case of a fermented food containing viable cells therein, it is extremely difficult to maintain its favorable taste and flavor, which the fermented food has immediately after its production, continuously during its storage and distribution period. For example, yogurt which features the inclusion of viable cells therein is accompanied by the taste- and flavor-related drawback that its acidity increases during its storage and distribution period and its sour taste becomes stronger. A variety of methods have heretofore been attempted with a view toward preventing an acidity increase during storage of yogurt. These methods were however all impractical because they were unable to bring about sufficient effects, rendered the production process extremely complex and cumbersome, or resulted in a very high production cost.

Fermented foods such as yogurt contain viable cells therein as described above. These viable cells remain active during storage so that they may deteriorate the taste and flavor of such fermented foods during their storage.

To avoid deterioration in taste and flavor of fermented foods by such a cause, it is most preferable to inhibit the activity of the bacteria, said activity being a cause for the deterioration in taste and flavor, without modifying their conventional production steps.

Yogurt contains *Lactobacillus delbrueckii* subsp. *bulgaricus* as principal starter bacteria together with one or more thermophilic bacteria. The former bacteria are a primary cause for acidity increase at least during the storage and distribution period. It is hence possible to effectively avoid deterioration in quality due to acidity increase during the storage and distribution period if the growth of the former bacteria can be suppressed and the production of the acid by the bacteria strain can be minimized directly.

SUMMARY OF THE INVENTION

With the foregoing in view, the present inventors proceeded with an investigation on possible interaction between bacteria, which can serve as starters for fermented foods, and the growth of thermophilic bacteria. In the course of the investigation, it was found that fresh milk contains thermophilic bacteria which inhibit the growth of such starters. The present inventors then succeeded in isolating and identifying the thermophilic bacteria.

A further investigation of the thermophilic bacteria so isolated has revealed that these bacteria are novel and produce an antibacterial substance, leading to completion of the present invention.

An object of the present invention is to provide novel lactic acid bacteria which produce an antibacterial substance.

Another object of the present invention is to provide the antibacterial substance produced by the novel lactic acid bacteria.

A further object of the present invention is to provide a starter for fermented milk, said starter comprising the novel lactic acid bacteria.

A still further object of the present invention is to provide a process for producing fermented milk by using such a starter, said fermented milk featuring reduced acidity increase during its storage or transportation.

In one aspect of the present invention, there is thus provided a novel lactic acid bacteria isolated from milk and belonging to the genus *Streptococcus salivarius* subsp. *thermophilus*.

In another aspect of the present invention, there is also provided an antibacterial substance available from a precipitate of ammonium sulfate fractionation by culturing the lactic acid bacteria in a liquid culture medium and then subjecting the resultant culture to ammonium sulfate fractionation.

In a further aspect of the present invention, there is also provided a starter for fermented milk, said starter comprising the above lactic acid bacteria.

In a still further aspect of the present invention, there is also provided a process for producing fermented milk by using the above starter, said fermented milk featuring reduced acidity increase during its storage or transportation.

BRIEF DESCRIPTION OF THE DRAWINGS

FIG. 1 diagrammatically illustrates the antibacterial activities of a culture medium and the absorbance at the wavelength of 660 nm as a function of the culture time of the lactic acid bacteria according to the present invention, in which dots and circles indicate antibacterial activities and absorbance, respectively; and FIG. 2 diagrammatically shows an increase in acidity when the yogurt produced in Example 5 was stored at 10° C.

DETAILED DESCRIPTION OF THE INVENTION

The novel lactic acid bacteria according to the present invention was isolated from milk in the following manner.

Fresh milk was added to the concentration of 5% in a 10% (w/w) reconstituted skim milk medium which had been pasteurized at 115° C. for 15 minutes, followed by incubation at 40°–45° C. until coagulation. After coagulation was repeated twice to three times in the similar manner, an inoculating loopful of the resultant culture was collected, smeared on the agar medium [1.0% (w/w) soytone, 0.5% (w/w) yeast extract, 1.0% (w/w) lactose, 1.0% (w/w) sodium succinate, 0.2% (w/w) potassium dihydrogenphosphate, 0.2% (w/w) dipotassium hydrogenphosphate, 1.5% (w/w) agar powder; pH 6.8; hereinafter abbreviated as "SYL agar medium"] proposed by Irie et al. in Journal of Japanese Society of Agricultural Chemistry, 45, 423 (1971), and then cultured at 40° C. for 2–3 days. From numerous colonies so formed, strains were isolated. Using as test bacteria *Lactobacillus helveticus* subsp. *jugurty* which is used as a starter for fermented milk, the thus-isolated strains were tested by cup method in which SYL agar medium was used. The strains which exhibited antibacterial activities were selected. With respect to each of the cell strains so selected, the antibacterial activities were tested by a broth dilution method in which the culture medium [1.0% (w/w) soytone, 0.5% (w/w) yeast extract, 1.0% (w/w) lactose, 1.0% (w/w) sodium succinate, 0.2% (w/w) potassium dihydrogenphosphate, 0.2% (w/w) dipotassium hydrogenphosphate; pH 6.8; hereinafter abbreviated as "SYL medium"] proposed by Irie et al. in "Journal of Japanese Society of Agricultural Chemistry", 45 423 (1971)]. One of the strains, on which antibacterial activities were observed, was selected and stored.

With respect to the bacteria so selected, its mycological characteristics were tested. It was found to have the following characteristics:

(a) Morphology

The following morphology is exhibited in SYL medium:
(1) Cell shape and size:
Micrococci or diplococci. The cell size ranges from 0.8 μm to 1.0 μm.
(2) Gram staining: Positive.

(b) The following physiological properties are shown:

| | | | |
|---|---|---|---|
| (1) | Coagulation of skim milk | | + |
| (2) | Production of ammonia | | − |
| (3) | Production of catalase | | − |
| (4) | Growth range: | | |
| | (i) | Temperature | |
| | | 10° C. growth | − |
| | | 45° C. growth | + |
| | (ii) | Salt resistance | |
| | | 2% salt resistance | + |
| | | 6.5% salt resistance | − |
| | (iii) | pH | |
| | | pH 9.6 resistance | − |
| | (iv) | 0.1% methylene blue resistance | − |
| (5) | VP test | | − |
| (6) | Carbohydrate fermentation ability: | | |

-continued

| | | | |
|---|---|---|---|
| | (i) | Arabinose | − |
| | (ii) | Xylose | − |
| | (iii) | Glucose | + |
| | (iv) | Mannose | + |
| | (v) | Fructose | + |
| | (vi) | Galactose | + |
| | (vii) | Maltose | − |
| | (viii) | Sucrose | + |
| | (ix) | Lactose | + |
| | (x) | Trehalose | − |
| | (xi) | Sorbitol | − |
| | (xii) | Mannitol | − |
| | (xiii) | Glycerol | − |
| | (xiv) | Starch | − |
| | (xv) | Raffinose | − |
| | (xvi) | Salicin | − |
| | (xvii) | Cellobiose | − |
| | (xviii) | Dextrin | − |
| | (xix) | Inulin | − |
| (7) | Production of antibacterial substance | | + |

Based on the above mycological characteristics, the above bacteria were classified in accordance with Bergey's Manual of Systematic Bacteriology, Vol. 2 (compiled jointly by P. H. A. Sneath, N. S. Mair, M. E. Sharpe and J. G. Holt, pp1069–1070, William & Wilkins, Baltimore U.S.A., 1986). As a result, the bacteria was identified as bacteria belonging to the genus *Streptococcus salivarius* subsp. *thermophilus* and, in view of the production of the antibacterial substance, as a novel strain different from the conventional bacteria.

The present inventors therefore named this bacteria as *Streptococcus salivarius* subsp. *thermophilus* SBT 1277, and deposited December 11, 1989 with Fermentation Research Institute, Agency of Industrial Science and Technology, Ministry of International Trade and Industry, Government of Japan, to which the deposit number FERM P-11155 was allotted. The deposit of the bacteria was then transferred to international deposit, so that FERM BP-3234 was allotted.

This bacteria can be transformed by general transformation treatment, for example, radiation such as ultraviolet rays or a chemical reagent such as N-methyl-N'-nitro-N-nitrosoguanine (NTG). Such variants of these bacteria are embraced by the present invention.

This invention also relates to the antibacterial substance produced by the above lactic acid bacteria according to the present invention or by any one of the above variants of the present invention. The antibacterial substance according to the present invention is a peptide or protein or a conjugate thereof, which can be obtained from a precipitate fractionated with ammonium sulfate at 30–70% saturation by culturing the lactic acid bacteria or variant in SYL medium, for example, at 30° C. for 24 hours and subjecting the resultant culture to ammonium sulfate fractionation.

The antibacterial spectrum of the antibacterial substance according to the present invention is shown in Table 1.

TABLE 1

| Bacteria tested | MIC* (units/ml) |
|---|---|
| *Bacillus cereus* SBT 3051 | >32 |
| *Bacillus stearothermophilus* SBT 3012 | 1 |
| *Bacillus subtilis* SBT 3011 | 32 |
| *Bifidobacteria longum* SBT 2928 | 8 |
| *Bifidobacteria breve* subsp. *breve* SBT 2803 | 4 |
| *Escherichia coli* SBT 3057 | >32 |
| *Lactococcus lactis* subsp. *lactis* SBT 1219 | >32 |

TABLE 1-continued

| Bacteria tested | MIC* (units/ml) |
|---|---|
| Lactococcus lactis subsp. diacetylactis SBT 1255B | >32 |
| Lactococcus lactis subsp. cremoris SBT 1323 | >32 |
| Lactobacillus acidophilus SBT 2062 | 32 |
| Lactobacillus delbrueckii subsp. bulgaricus MRC-32-R | 4 |
| Lactobacillus casei SBT 2209 | >32 |
| Lactobacillus helveticus subsp. jugurti SBT 2161 | 1 |
| Pseudomonas aeruginosa SBT 3267 | 32 |
| Pseudomonas fluorescens SBT 3224 | 16 |
| Pseudomonas fragi SBT 3227 | 32 |
| Salmonella typhimurium SBT 3075 | >32 |
| Sarcina lutea SBT 3013 | >32 |
| Serratia marcescens SBT 3155 | >32 |
| Staphylococcus aureus SBT 3159 | 4 |
| Streptococcus faecalis SBT 1120 | >32 |
| Streptococcus faecium SBT 1155 | >32 |
| Streptococcus mutans SBT 1454 | >32 |
| Streptococcus salivarius subsp. thermophilus SBT 0137 | 2 |

*MIC: Minimum inhibitory concentration.
1 Unit: Weight of the antibacterial substance required to inhibit growth of $10^6$ cells of Lactobacillus helveticus subsp. jugurty.

As is understood from Table 1, the antibacterial substance shows antibacterial activities against gram-positive bacteria only and has a narrow antibacterial spectrum, so that the antibacterial substance exhibits properties of typical bacteriocins.

The antibacterial spectrum of Table 1 was prepared by the following method.

On a commercially-available, sterilized 96-well microplate, 200 μl portions of a liquid medium inoculated with 1% of one of the bacteria to be tested, said medium being suited for the growth of the bacteria, were added to and mixed with 50 μl portions of samples of the doubling dilution system of the precipitate fractionated with ammonium sulfate at 30–70% saturation, respectively. The bacteria were then cultured at predetermined temperature suitable for the growth of the particular bacteria. The growth of the particular bacteria in each culture was qualitatively judged. The lowest one of the concentrations of the ammonium-sulfate-fractionated precipitate added to the cultures in which the growth was suppressed was recorded as the minimum inhibitory concentration.

In addition, the thermal stability of the above-described ammonium-sulfate-fractionated precipitate and its digestion by trypsin and phospholipase D were measured. The measurement data were compared with the corresponding data of conventional bacteriocins (nisin, lactostrepcin, and diplococcin) known to be produced by streptococci. The results are summarized in Table 2.

TABLE 2

| | Properties of antibacterial substance | | |
|---|---|---|---|
| Antibacterial substance | Trypsin digestability | Phospholipase D digestability | Heat treatment (100° C., 30 min, pH 8.0) |
| Antibacterial substance of the invention | S* | R** | R |
| Nisin | R | — | S |
| Lactostrepcin | S | S | — |
| Diplococcin | S | — | S |

*S: sensitive.
**R: resistant.

As is readily envisaged from Table 2, the antibacterial substance of the present invention shows different properties in heat treatment, trypsin digestability and phospholipase D digestability compared with the conventionally-known bacteriocins produced by streptococci. Accordingly, the antibacterial substance of the present invention can be undoubtedly judged as a novel substance.

Incidentally, the heat treatment test, the trypsin digestability test and the phospholipase D digestability test were conducted by the following methods.

1) Heat resistance test:

The precipitate fractionated with ammonium sulfate was dissolved in a buffer of pH 8.0 and then heated for 30 minutes in a boiling bath. After the solution was cooled, the antibacterial substance was determined "resistant" or "sensitive" depending on the "presence" or "absence" of an inhibited zone in accordance with the cup method* in which Lactobacillus helveticus subsp. jugurty was used as an indicator strain of an antibacterial test. 2) Trypsin digestability and phospholipase D digestability:

The precipitate fractionated with ammonium sulfate was dissolved in a buffer of pH 7.0. Portions of the resultant solution were added with the enzymes, trypsin and phospholipase D, respectively to give the final concentration of 5 mg/ml. The resulting mixtures were incubated at 25° C. for 1 hour. Using the cup method* in which Lactobacillus helveticus subsp. jugurty was used as test bacteria, the antibacterial substance was determined "resistant" or "sensitive" depending on the "presence" or "absence" of an inhibited zone.

* Cup method:

A cup cylinder is placed on an agar plate in which Lactobacillus helveticus subsp. jugurty has been mixed and diluted in advance (inoculum size: 1%). A sample (100 μl) is placed in the cup cylinder, followed by incubation at 37° C. for 16 hours. The diameter of an inhibited zone is then measured.

The antibacterial substance according to the present invention can be obtained by the process described above. It is a peptide or protein or a conjugate thereof, is digested by trypsin but not by phospholipase D, and exhibits stability even after heating at 100° C. and pH 8.0 for 30 minutes.

It is to be noted that mixtures comprising the antibacterial substance are also embraced by the present invention. Exemplary mixtures which comprise the antibacterial substance include culture media, cultures and supernatants thereof, and the like.

The antibacterial substance of the present invention and mixtures comprising the same can be used as preservatives for beverages, foods, feed and the like, if necessary, after application of sterilization treatment.

This invention also relates to starters for fermented milk, said starters comprising the lactic acid bacteria of the present invention or any one of the variants of the present invention and also to fermented milk obtained using such starters.

According to the present invention, the above lactic acid bacteria is inoculated to and cultured in sterilized skim milk. The resultant culture is used as a starter for fermented milk. Combined use of this starter for fermented milk together with lactic acid bacteria heretofore employed as a starter for yogurt, for example, thermophilic bacteria, Lactobacillus delbrueckii subsp. bulgaricus, Lactobacillus helveticus subsp. jugurty or Bifidobacteria breve subsp. breve makes it possible to inhibit the growth of the bacteria by the antibacterial substance produced by the starter. It is therefore possible to reduce quality reduction of a fermented food containing one or more of such strains therein, which quality reduction is caused by excessive production of the acid during the storage and distribution period of the fermented food. Especially, among thermophilic bacteria and *Lactobacillus delbrueckii* subsp. *bulgaricus* which are commonly employed as starters for fermented milk, the growth of the latter bacteria as cause for quality deterioration during a storage and distribution period can be suppressed. It is therefore possible to improve the quality of fermented milk.

In addition, the strain of the lactic acid bacteria and its variants according to the present invention can be used not only as starters for yogurt but also as fermentation regulators, for example, to improve the quality of milk products such as sour milk beverages and fermented milk. The starters according to the present invention, which are suited for use in the production of fermented milk, can also be used as such fermentation regulators.

Illustrative of the fermented milk which can be produced by the process of the present invention include yogurt (both hard-type and soft-type) and sour milk beverages. Upon production of fermented milk in the present invention, the lactic acid bacteria of the present invention and one of the above-described conventional lactic acid bacteria—which have been employed for the production of fermented milk—are inoculated as starters either individually and successively or in combination to a raw material for fermented milk, followed by fermentation. The raw material for the fermented milk, the amounts of the starters and the conditions for the fermentation can chosen as in the conventional processes.

The present invention will hereinafter be described more specifically by the following examples. It should however be borne in mind that the present invention is not limited to or by the following examples.

Example 1

SYL medium (50 l) was sterilized at 121° C. for 15 minutes and then cooled to 30° C. A precultured broth (500 ml) of the lactic acid bacteria according to the present invention was inoculated to the medium, followed by incubation at 30° C. for 24 hours. After the incubation, the resultant culture was cooled to 4° C. Cells were collected at 3,000 rpm by a centrifugator, whereby the lactic acid bacteria of the present invention was obtained (yield: 1,174 g as wet cells).

Example 2

SYL medium (16 l) was sterilized at 121° C. for 15 minutes and then cooled to 30° C. A precultured broth (160 ml) of the lactic acid bacteria according to the present invention, antibacterial-substance-producing bacteria, was inoculated to the medium, followed by incubation at 30° C. for 24 hours. Immediately after the incubation, the resultant culture was cooled to 4° C. Cells were removed at 3,000 rpm by a centrifugator, whereby a supernatant containing the antibacterial substance was obtained (yield: 14.9 l). Its antibacterial activities were 8 units per ml so that the overall antibacterial activities were 119,200 units. Incidentally, 1 unit is defined as the weight of the antibacterial substance required to inhibit growth of $10^6$ cells of *Lactobacillus helveticus* subsp. *jugurty*.

In the present invention, a relationship between culture time and the antibacterial activities of a culture can be expressed as shown in FIG. 1. The antibacterial activities abruptly increased after 6 hours of incubation and reached a maximum around 8 hours of incubation. This behavior was slower compared with the absorbance at the wavelength of 660 nm, which indicated the amount of cells.

Example 3

Sterilized at 121° C. for 15 minutes was Elliker agar medium [2% (w/w) tryptone, 0.5% w/w yeast extract, 0.25% (w/w) gelatin, 0.5% (w/w) dextrose, 0.5% (w/w) lactose, 0.5% (w/w) sucrose, 0.4% (w/w) sodium chloride, 0.15% (w/w) sodium acetate, 0.05% (w/w) ascorbic acid, 1.5% (w/w) agar; pH 6.8). While the medium was in a liquid state, the sterilized medium was poured as 20 ml portions in sterilized Petri dishes. The medium was then cooled and solidified, whereby agar plates were prepared. The lactic acid bacteria of the present invention, which had been cultured in SYL medium, was smeared in the form of a line by an inoculating loop on each of the agar plates, and was then cultured at 30° C. for 24 hours to allow it to produce the antibacterial substance. The agar plates were exposed for 1 hour to ultraviolet rays from an ultraviolet sterilization lamp, so that the bacteria thus smeared was sterilized. Mixtures of 0.1 ml of test bacteria cultured in Elliker medium and Elliker soft agar medium [a culture medium obtained by adjusting the concentration of agar of Elliker agar medium to 0.7% (w/w)] cooled to 45° C. subsequent to its melting were placed as a layer over the agar plates, respectively. The test bacteria consisted of 45 thermophilic bacteria strains used as starters for fermented milk and 27 *Lactobacillus delbrueckii* subsp. *bulgaricus* strains. The thus-overlayed agar plates were incubated at 37° C. for 24 hours, followed by the determination of the presence or absence of an inhibited band. As a result, such an inhibited band was observed on 43 thermophilic bacteria strains and 7 *Lactobacillus delbrueckii* subsp. *bulgaricus* strains.

Example 4

The lactic acid bacteria of the present invention were inoculated in pasteurized skim milk and then cultured to provide Starter A for fermented milk. A mixed starter of commercial thermophilic bacteria and *Lactobacillus delbrueckii* subsp. *bulgaricus* were inoculated in pasteurized skim milk and then cultured to provide Starter B for fermented milk. Both the starters were inoculated to the concentration of 1.5%, each, to the same pasteurized yogurt mix (pasteurized milk enriched with powdered skim milk), followed by incubation at 42° C. until the lactic acid acidity reached 0.8%. The culture was immediately cooled, whereby the culture containing the lactic acid bacteria of this invention was obtained as yogurt.

The yogurt of this example was free from an acidity increase after its production, thereby permitting stable storage.

Example 5

*Streptococcus salivarius* subsp. *thermophilus* SBT 1277 according to the present invention and *Lactobacillus delbrueckii* subsp. *bulgaricus* SBT-2118B (MRC-32-RO) were inoculated to the concentration of 1.5%, each, to a yogurt mix which consisted of fresh milk, powdered skim milk and sugar, followed by incubation at 42° C. until the acidity reached 0.75% so that yogurt was obtained. The yogurt was refrigerated at 10° C. and stored for 14 days. The acidity increase during the storage period is plotted in FIG. 2.

As is understood from FIG. 2, substantially no acidity increase was observed at 10° C.

The present invention provides novel lactic acid bacteria belonging to the genus *Streptococcus salivarius* subsp. *thermophilus*. The novel lactic acid bacteria according to the present invention produce an antibacterial substance of the bacteriocin type. This antibacterial substance can be used as a preservative for beverages, foods, feed and the like.

Further, fermented milk can be produced using the lactic acid bacteria of the present invention as a starter. Especially, its use as a starter for yogurt can suppress production of the acid during the storage and transportation of the resultant yogurt, thereby making it possible to prevent quality reduction of the yogurt due to excessive production of the acid.

What is claimed is:

1. A process for reducing the rise in acidity which occurs during storage or transportation of a fermented milk product produced by inoculating milk with a fermented milk starter containing a lactic acid producing bacteria, which comprises concurrently inoculating the milk with a fermented milk starter comprising *Streptococcus Salivarius* subsp. *thermophilus* SBT 1277 (FERM BP-3234) or a radiation or chemically transformed variant thereof in an amount sufficient to inhibit the growth of grampositive bacteria in the fermented milk product which give rise to acidity during storage or distribution thereof; and thereafter concurrently culturing the fermentation milk starter.

2. The process of claim 1, wherein the lactic acid bacteria employed to form lactic acid comprises one or more lactic acid bacteria selected from the group consisting of *Lactobacillus delbrueckii* subsp. *bulgaricus, Lactobacillus helveticus* subsp. *jugurty* and *Bifidobacteria breve* subsp. *breve*.

3. The process of claim 1, wherein the fermented milk is a lactic acid fermentation beverage.

4. The process of claim 1, wherein the fermented milk is a lactic acid fermentation beverage.

5. A process according to claim 1, wherein the rise in level of acidity is thereby limited to at most 0.1%.

6. The process of claim 1, wherein the fermentation milk starter comprises *Streptococcus Salivarius* subsp. *thermophilus* SBT 1277.

7. The process of claim 1, wherein the *Streptococcus Salivarium* subsp. *thermophilus* SBT 1277 or a radiation or chemically transformed variant thereof inhibits the growth of *Lactobacillus bulgaricus, Bacillus stearothermophilus* or *Streptococcus thermophilus* bacteria or mixtures thereof.

8. The process of claim 1, wherein the radiation transformed variant of *Streptococcus Salivarium* subsp. *thermophilus* SBT 1277 is transformed by ultraviolet radiation and the chemically transformed variant of *Streptococcus Salivarium* subsp. *thermophilus* SBT 1277 is transformed by the chemical reagent N-methyl-N'-nitro-N-nitrosoguanine.

* * * * *